US00PP31985P2

(12) United States Plant Patent
Winslow et al.

(10) Patent No.: US PP31,985 P2
(45) Date of Patent: Jul. 14, 2020

(54) ***BIDENS* PLANT NAMED 'BALEEHEDI'**

(50) Latin Name: *Bidens ferulifolia*
Varietal Denomination: Baleehedi

(71) Applicant: Ball Horticultural Company, West Chicago, IL (US)

(72) Inventors: Benjamin K. Winslow, Austin, TX (US); Laura L. Masor, Grover Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 16/501,963

(22) Filed: Jul. 10, 2019

(51) Int. Cl.
*A01H 5/02* (2018.01)
*A01H 6/14* (2018.01)

(52) U.S. Cl.
USPC ..... Plt./410
CPC ..... *A01H 6/14* (2018.05)

(58) Field of Classification Search
USPC ..... Plt./410
CPC ..... A01H 6/14
See application file for complete search history.

*Primary Examiner* — Anne Marie Grunberg
(74) *Attorney, Agent, or Firm* — Audrey Charles

(57) ABSTRACT

A new and distinct cultivar of *Bidens* plant named 'Baleehedi', characterized by its dark red-orange and yellow-orange bicolored inflorescences, medium green-colored foliage, and moderately vigorous, and semi-upright growth habit, is disclosed.

1 Drawing Sheet

Latin name of genus and species of plant claimed: *Bidens ferulifolia.*

Variety denomination: 'Baleehedi'.

BACKGROUND OF THE INVENTION

The present invention relates to a new and distinct cultivar of *Bidens* plant botanically known as *Bidens ferulifolia* and hereinafter referred to by the cultivar name 'Baleehedi'.

The new cultivar originated in a controlled breeding program in Arroyo Grande, Calif. during November 2015. The objective of the breeding program was the development *Bidens* cultivars that have large inflorescences with attractive coloration and moderately vigorous, semi-upright growth habit.

The new *Bidens* cultivar was the result of a self-pollination of the proprietary *Bidens ferulifolia* breeding selection coded 754-001, not patented, characterized by its medium red-colored flowers, medium green-colored foliage, and moderately vigorous, spreading growth habit. The new cultivar was discovered and selected as a single flowering plant within the progeny of the above stated self-pollination during October 2016 in a controlled environment in Arroyo Grande, Calif.

Asexual reproduction of the new cultivar by terminal stem cuttings since October 2016 in Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Baleehedi' as a new and distinct cultivar of *Bidens* plant:

1. Dark red-orange and yellow-orange bicolored inflorescences;

2. Medium green-colored foliage;
3. Moderately vigorous, and semi-upright growth habit.

Plants of the new cultivar differ from plants of the parent primarily in having a bicolored inflorescence and more semi-upright growth habit.

Of the many commercially available *Bidens* cultivars, the most similar in comparison to the new cultivar is Timeless Blazing Glory 'DBIDBLAZGL', U.S. Plant Pat. No. 29,071. However, in side-by-side comparisons, plants of the new cultivar differ from plants of 'DBIDBLAZGL' in at least the following characteristics:

1. Plants of the new cultivar have larger diameter inflorescences than plants of 'DBIDBLAZGL'; and
2. Plants of the new cultivar have densely pubescent stems and peduncles unlike plants of 'DBIDBLAZGL'.

BRIEF DESCRIPTION OF THE PHOTOGRAPHS

The accompanying photographs show, as nearly true as it is reasonably possible to make the same in color illustrations of this type, typical inflorescence and foliage characteristics of the new cultivar. Colors in the photographs may differ slightly from the color values cited in the detailed description, which accurately describes the colors of 'Baleehedi'. The plants were approximately 5 months old and grown in 6-inch pots for approximately 20 weeks in a greenhouse in West Chicago, Ill. Plants were given one pinch approximately 2 weeks after transplant.

DETAILED BOTANICAL DESCRIPTION

Figure 1:
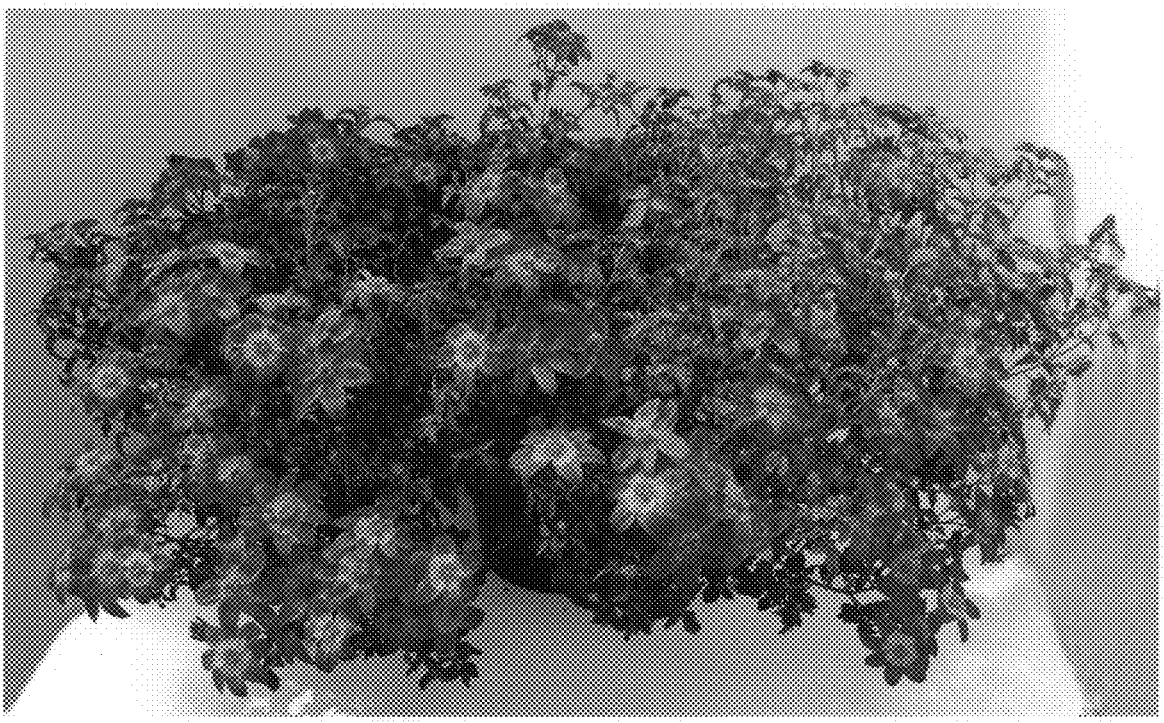
FIG. 1 illustrates a side view of the overall growth and flowering habit of 'Baleehedi'.
Figure 2:
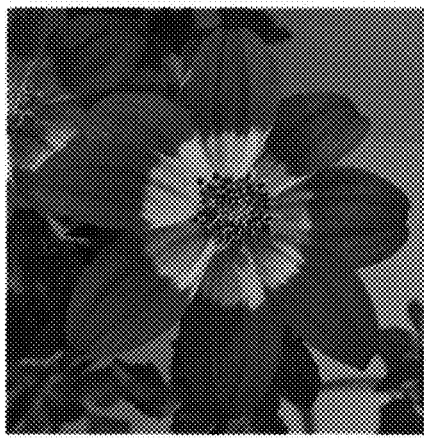
FIG. 2 illustrates a close-up view of an individual inflorescence of 'Baleehedi'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in June 2019 under natural light conditions in West Chicago, Ill.

The following descriptions and measurements describe approximately 5-month old plants produced from cuttings from stock plants and grown in a glass-covered greenhouse under conditions comparable to those used in commercial practice. The plants were grown in West Chicago, Ill. in 6-inch pots for approximately 20 weeks utilizing a soilless growth medium. Plants were given one pinch approximately 2 weeks after transplant. Greenhouse temperatures were maintained at approximately 67° F. to 72° F. (19° C. to 22° C.) during the day and approximately 65° F. to 68° F. (18° C. to 20° C.) during the night. Supplemental lighting was used. Measurements and numerical values represent averages of typical plants.

Botanical classification: *Bidens ferulifolia* 'Baleehedi'.

Parentage:

*Female and male parents*.—Proprietary *Bidens ferulifolia* breeding selection coded 754-001, not patented.

Propagation:

*Type cutting*.—Terminal stem.

*Time to initiate roots*.—Approximately 6 to 9 days.

*Time to produce a rooted cutting*.—Approximately 21 to 28 days.

*Root description*.—Fibrous, medium to thin in thickness.

*Rooting habit*.—Freely branching, dense.

Plant description:

*Commercial crop time*.—Approximately 5 to 7 weeks from a rooted cutting to finish in a 10 cm container.

*Growth habit and general appearance*.—Annual, moderately vigorous, and semi-upright.

*Size*.—Height from soil level to top of plant plane: Approximately 27.0 cm. Width: Approximately 82.0 cm.

*Branching habit*.—Freely branching, pinching improves lateral branching. Quantity of main branches per plant: Approximately 9 with approximately 12 lateral branches.

*Main branches*.—Strength: Strong. Aspect: Erect to 90° angle. Shape: Round in cross section. Length to base of inflorescence: Approximately 21.0 cm. Diameter: Approximately 3.0 mm to 6.0 mm. Length of central internode: Approximately 3.0 cm. Texture: Densely pubescent with minute hairs. Color of young stems: 146C. Color of mature stems: 146C with a heavy overlay of 187A.

Foliage description:

*General description*.—Form: Trifoliate. Arrangement: Opposite. Fragrance: None detected. Aspect: Petiole is acute angle to stem; blade is perpendicular to stem or downward turning.

*Leaves*.—Shape of leaf and leaflets: Ovate. Margin of leaf and leaflet: Laciniate. Apex of leaf and leaflet: Acuminate. Base of leaf and leaflet: Attenuate. Venation pattern: Pinnate. Length: Approximately 3.7 cm. Width: Approximately 3.0 cm. Length of terminal leaflet: Approximately 2.9 cm. Width of terminal leaflet: Approximately 1.6 cm. Length of lateral leaflet: Approximately 1.7 cm. Width of lateral leaflet: Approximately 1.1 cm. Texture of upper and lower surfaces: Sparsely pubescent. Color of upper surface: 137A with venation of 146D. Color of lower surface: Closest to 138B with venation of 138C. Length of rachis: Approximately 2.0 mm. Diameter of rachis: Approximately 1.5 mm. Texture of upper and lower surfaces of rachis: Moderately pubescent. Color of upper and lower surfaces of rachis: 146D with an overlay of 187A.

*Petiole*.—Length: Approximately 1.2 cm. Diameter: Approximately 2.0 mm. Texture of upper and lower surfaces: Moderately pubescent. Color of upper and lower surfaces: 146D with an overlay of 187A.

Flowering description:

*Flowering habit*.—'Baleehedi' is freely flowering under outdoor growing conditions with substantially continuous blooming from early spring through autumn.

*Lastingness of individual inflorescence on the plant*.—Approximately 3 to 4 weeks.

Inflorescence description:

*General description*.—Type: Solitary, composite. Shape: Radiant head. Aspect: Facing upward and outward. Arrangement: Terminal, held upright on strong peduncles. Fragrance: Slight. Quantity per plant: Approximately 175. Diameter: Approximately 4.5 cm. Depth: Approximately 1.0 cm.

*Peduncle*.—Strength: Strong. Aspect: Erect to approximately 45° from vertical. Length: Approximately 1.5 cm to 3.0 cm. Diameter: Approximately 1.5 mm. Texture: Densely pubescent with short appressed hairs. Color: 146C.

*Bud just before opening*.—Quantity per plant: Approximately 70. Shape: Globose. Diameter: Approximately 6.0 mm. Depth: Approximately 5.0 mm. Color: 151B.

*Ray florets*.—Quantity per inflorescence: Approximately 8, occasionally with one to three underdeveloped. Arrangement: In a single whorl, imbricate. Aspect: Perpendicular to disc, subtending with age. Shape: Ovate. Appearance: Dull. Margin: Entire. Apex: Three lobed. Base: Rounded. Length: Approximately 2.0 cm. Width: Approximately 1.0 cm. Texture of upper surface: Glabrous. Texture of lower surface: Glabrous, with two longitudinal ribs. Color of upper surface when first open: N34A with an overlay of 183A in center, base of 17A. Color of lower surface when first open: 166C to 166D with base of 17C. Color of upper surface when fully open 172A to 172B, base of 17B; with age base has an overlay of 172B. Color of lower surface when fully open: 17C with an overlay of 166C to 166D.

*Disc florets*.—Disc diameter: Approximately 1.0 cm. Quantity per inflorescence: Approximately 80. Arrangement: Spirally arranged in center of inflorescence. Shape: Tubular. Margin of free portion: Entire. Apex: Five acute tips. Base: Fused into a tube. Length: Approximately 8.0 mm. Diameter: Approximately 1.0 mm. Texture of inner surface: Glabrous. Texture of outer surface: Sparsely pubescent near base. Color of upper or inner surface when first and fully open: 17C. Color of lower or outer surface when first and fully open: 145D with upper half of 17C and tips of 17B.

*Receptacle*.—Shape: Flat disc. Diameter: Approximately 4.0 mm. Color: 145D.

*Phyllaries*.—Quantity per inflorescence Approximately 9. Arrangement: In a single whorl. Appearance: Dull. Shape: Lanceolate. Margin: Entire. Apex: Acute. Base: Truncate. Length: Approximately 8.0 mm. Width: Approximately 1.0 mm. Texture of upper or inner surface: Densely pubescent with short hairs. Texture of lower or outer surface: Densely pubescent with short hairs. Color of upper and lower surfaces: 137A.

*Reproductive organs*.—Androecium: Present on disc florets only. Stamen quantity: 5 per floret. Anther shape: Oblong, basifixed. Anther length: Approximately 2.0 mm. Anther color: 166A. Filament length: Approximately 3.0 mm. Filament color: Closest to NN155A, translucent. Pollen amount: Abundant. Pollen color: 23A. Gynoecium: Present on disc florets only. Pistil quantity: 1 per floret. Pistil length: Approximately 8.0 mm. Stigma shape: Bifurcate, strongly curled. Stigma length: Approximately 1.0 mm, 2.0 mm if straightened. Stigma color: 17B. Style length: Approximately 5.0 mm. Style color: 154D, translucent. Ovary length: Approximately 2.0 mm. Ovary color: 145D.

Seed and fruit production: Neither seed nor fruit production has been observed.

Disease and pest resistance: Resistance to pathogens and pests common to *Bidens* has not been observed.

What is claimed is:

1. A new and distinct cultivar of *Bidens* plant named 'Baleehedi', substantially as herein illustrated and described.

* * * * *